(12) United States Patent
Gilles (10) Patent No.: US 9,046,534 B2
(45) Date of Patent: Jun. 2, 2015

(54) METHODS AND SYSTEMS FOR IDENTIFYING AND TREATING ANTI-PROGESTIN SENSITIVE TUMORS (71) Applicant: Erard Gilles, Bridgewater, NJ (US)

(72) Inventor: Erard Gilles, Bridgewater, NJ (US)

(73) Assignee: INVIVIS PHARMACEUTICALS INC., Bridgewater, NJ (US)

(*) Notice: Subject to any disclaimer, the term of this patent is extended or adjusted under 35 U.S.C. 154(b) by 0 days.

(21) Appl. No.: 13/644,872

(22) Filed: Oct. 4, 2012

(65) Prior Publication Data
US 2013/0095170 A1 Apr. 18, 2013

Related U.S. Application Data (60) Provisional application No. 61/542,931, filed on Oct. 4, 2011.

(51) Int. Cl.

| A61K 31/56 | (2006.01) |
|---|---|
| G01N 33/74 | (2006.01) |
| C12Q 1/02 | (2006.01) |
| G01N 33/50 | (2006.01) |
| G01N 33/574 | (2006.01) |
| A61K 45/06 | (2006.01) |
| A61K 31/4152 | (2006.01) |
| A61K 31/567 | (2006.01) |
| A61K 31/57 | (2006.01) |
| A61K 31/575 | (2006.01) |
| A61K 31/557 | (2006.01) |

(52) U.S. Cl.
CPC ............ *G01N 33/743* (2013.01); *A61K 31/557* (2013.01); *C12Q 1/025* (2013.01); *G01N 33/5011* (2013.01); *G01N 33/574* (2013.01); *A61K 45/06* (2013.01); *A61K 31/4152* (2013.01); *A61K 31/567* (2013.01); *A61K 31/57* (2013.01); *A61K 31/575* (2013.01)

(58) Field of Classification Search
CPC ................................. C12Q 1/00; A61K 31/557
USPC .......................................................... 514/181
See application file for complete search history.

(56) References Cited

U.S. PATENT DOCUMENTS

| 4,742,000 A | 5/1988 | Greene |
| 5,283,190 A | 2/1994 | Traish et al. |
| 2004/0072811 A1 | 4/2004 | Hoffmann et al. |
| 2004/0121304 A1 | 6/2004 | Fuhrmann et al. |
| 2011/0053900 A1 | 3/2011 | Podolski et al. |

OTHER PUBLICATIONS

Etreby et al., "Antitumor Activity of Mifepristone in the Human LNCaP, LNCaP-C4, and LNCaP-C4-2 Prostate Cancer Models in Nude Mice", The Prostate, vol. 42, No. 2, pp. 99-106 (2000).*
Arnett-Mansfield et al., "Focal Subnuclear Distribution of Progesterone Receptor is Ligand Dependent and Associated with Transcriptional Activity," Molecular Endocrinology, vol. 2, No. 1, pp. 14-29, 2007.

* cited by examiner

*Primary Examiner* — Kevin E Weddington (74) *Attorney, Agent, or Firm* — VLP Law Group LLP; Jeremy A. Cubert (57) ABSTRACT

Methods and systems for identifying and treating a patient suspected of having a tumor susceptible to growth inhibition by anti-progestins are provided. The degree of focal distribution of the progesterone receptor can be used to identify tumors susceptible to treatment with anti-progestin therapy.

12 Claims, 4 Drawing Sheets

D Pattern  A Pattern

METHODS AND SYSTEMS FOR IDENTIFYING AND TREATING ANTI-PROGESTIN SENSITIVE TUMORS

This application claims priority to U.S. Provisional Patent No. 61/542,931, filed on Oct. 4, 2011, the disclosure of which is incorporated by reference herein in its entirety.

BACKGROUND

The progesterone receptor (PR) is present in cells in two major isoforms, PR-A and PR-B. In the presence of a bound progestin ligand, such as progesterone, the PR is phosphorylated at specific sites, dimerizes, forms a complex with a number of different cellular elements (e.g., p300 and the steroid receptor coactivator), and binds to specific DNA sequences known as progesterone responsive elements (PREs) to initiate DNA transcription into RNA. The PR-ligand complex also attracts numerous other co-activators and co-repressors, which form the cellular elements which in turn transcribe particular genes. These PR complexes (also referred to as foci) can be visualized in the nuclei of cells which contain the progesterone receptor as fluorescent aggregates using immunohistofluorescence techniques and as dense and dark stained nuclear aggregates using the immunohistochemistry techniques described in this patent.

In premenopausal women, during the proliferative phase (the first part of the menstrual cycle) when estrogen is the dominant hormone and progesterone is minimally secreted, staining of normal endometrial cells for PR-A and PR-B (e.g., using immunofluorescent techniques and confocal microscopy) reveals a diffuse progesterone receptor nuclear staining pattern. In the secretory phase (the second part of the menstrual cycle) when progesterone is the dominant hormone, using the same immunofluorescent techniques and confocal microscopy, staining for PR-A and PR-B appears as readily detectable fluorescent nuclear foci.

RNA transcription inhibitors have been shown to prevent formation of PR foci, and 26S proteasome inhibitors have been shown to disrupt the PR nuclear foci. It is therefore believed that the presence of PR foci in cells corresponds to active transcriptional complexes, and indicates the activation of the PR and subsequent gene expression. Conversely, diffuse nuclear staining or the absence of PR foci indicates the presence of PR which is transcriptionally inactive. Upon exposure of normal breast and endometrium tissues (which are physiologically responsive to progesterone) to progestin ligands, a change from a diffuse nuclear staining pattern to focal subnuclear structures can be observed, indicating the activation of the progesterone receptor.

Whereas estrogens are mitogenic (e.g., cause cellular proliferation) for normal breast epithelial and endometrial cells, the effects of progestins are more complex. In the endometrium, progestins inhibit estrogen-induced cell cycle progression early in the $G_1$ phase, whereas in the breast progestins may both stimulate and inhibit proliferation. In normal breast tissue biopsies it has been shown that proliferative activity is stimulated by progesterone (Am J Obstet Gynecol, 1997). This complexity has led to confounding experimental observations in breast cancer. For example, progestogens appear to have a direct proliferative effect on breast cancer cell in vitro when phenol red-free media is used. H. J. Kloosterboer, J. Steroid Biochem. Molec. Biol. Vol. 49, No. 4-6, pp. 311-318, 1994. However, when the same contraceptive progestogens that induced proliferation in breast cancer cell lines were studied in an estrogen-dependent DMBA rat breast cancer model, these progestogens inhibited tumor progression. Id. It has been shown recently that many such in vitro experimental models are inadequate. See, e.g., Lange C. et al. Progesterone Receptor Action: Translating Studies in Breast Cancer Models to Clinical Insights. Chapter 7 in Innovative Endocrinology of Cancer; 94-111 (2010). While progesterone-induced proliferation has been shown in these experimental models, the majority of proliferating cells were not expressing the PR. Thus, these models do not necessarily predict the efficacy of treatment with antiprogestins.

Malignant cells also exhibit nuclear PR foci, but they are different in size and composition from the foci of normal cells. PR foci observed in cancer indicate a specific role for the PR which is pertinent to the malignant nature of the cells. For example, the genes activated by the PR in malignant (cancer) breast cells are different than the genes activated by the PR in normal breast cells; in endometrial cancers PR foci, but not PR levels, are associated with malignant characteristics; foci in cancer cells are larger, which may be due to alterations in the chromatin remodeling which are common in cancer, and; PR foci in breast cancer are observed regardless of hormonal status (e.g., in the presence and absence of circulating progesterone in premenopausal and post-menopausal women respectively). PR foci have been observed (e.g., using immunofluorescent techniques and confocal microscopy) in the tumor cells of approximately 50% of PR-receptor positive human breast cancer biopsies. Other patient's tumor samples exhibited a diffuse PR nuclear staining pattern in the tumor cells using immunofluorescent techniques and confocal microscopy, indicative of a non-activated or non-functional form of the PR.

The majority of breast cancers can be treated with hormonal treatments (i.e., anti-estrogens or aromatase inhibitors), which are currently some of the most effective medications used in breast cancer therapy. Hormonal treatment is usually indicated based on the identification of hormone receptors within the cancer cells. Onapristone (ONA) is an anti-progestin drug which was originally developed for contraceptive use. However, it has demonstrated substantial activity in advanced breast cancer, with a 10% response rate in a study of 101 poor prognosis patients with breast cancer in whom prior hormonal therapy had failed (e.g., breast cancer progressed despite the patient receiving the antiestrogen tamoxifen). In a small breast cancer study using ONA as a first line hormone treatment, ONA produced a 56% objective response rate, an efficacy in the upper range of the best available treatments in this disease. ONA binds to the PR, does not induce PR phosphorylation and does not allow the PR to dimerize. The PR-ONA complex binds weakly, or not at all, to its target DNA segment and therefore does not activate the chromatin remodeling which is a necessary process for DNA transcription. In in vitro systems, ONA has been shown to reverse the PR nuclear aggregates produced by binding of an artificial ligand to the PR. Gene activation studies have consistently shown that, while progestins and other anti-progestins activate progesterone responsive genes, ONA has minimal activation (i.e., 3 genes).

In addition, ONA is a pure PR antagonist at concentrations which can be physiologically achieved. ONA does not interfere with other steroid receptors and does not increase estrogen secretion in human subjects, which is an undesirable side-effect for breast cancer therapy exhibited by other anti-progestins such as mifepristone.

While onapristone has previously been investigated as a potential therapeutic agent for breast cancer, its development was stopped due to toxicity concerns. Robertson et al., *Onapristone, a Progesterone Receptor Antagonist, as First-line Therapy in Primary Breast Cancer* European J. of Cancer 35(2) 214-218 (1999). It is important to identify the subset of the patients with tumors most likely to respond and equally as important to identify the subset of the patients with tumors least likely to respond to treatment with ONA and other anti-progestins. Identifying these subsets of patients will allow those patients with APF access to a potentially effective cancer treatment and will avoid exposing patients with those cancers for which ONA or other anti-progestins may not provide benefit to unnecessary toxicity.

Currently, only the presence or absence of the estrogen or progesterone receptor is considered when making therapeutic decisions on whether to use an endocrine treatment in certain cancers (e.g., breast cancer). Accordingly, conventional assays for PR classify the tumors from patients with cancer into two categories: PR-positive or PR-negative. One type of assay quantitates the amount of PR per total protein of the cell. These methods can be automated and are quantitative, but are not satisfactory with respect to accuracy, sensitivity and analysis of cellular subnuclear receptor structures. A second type of assay includes immunohistochemical methods using formalin fixed tissue specimens and fluorescent or chromophore labeled monoclonal antibodies targeting the receptor (either an antibody for each of PR-A and PR-B, or a single antibody that recognizes both). With immunohistochemical methods, any microscopically detectable nuclear staining reaction in more than a certain percentage of cells (typically ≥1%), is reported as being PR positive as per professional society guidelines. Typically, a clinical cut off of ≥10% ER or PR positive cells is used to make therapeutic decisions regarding the use of anti-hormone treatments. No consideration is given to the pattern of cellular or nuclear staining. Relative staining intensity (i.e., low, medium, or high) is also use as a qualitative measure of hormone receptor positivity. This second type of assay is more labor intensive and it is not standardized. Typically, low magnification microscopic examination is used for the IHC analysis to identify the presence of the hormone receptor (either estrogen receptor (ER) or PR). Using conventional methods, no analysis of cellular distribution is done other then an estimate of the percentage of the tumor cells expressing the identified hormone receptor. Analysis of the subnuclear distribution pattern of the PR requires high powered microscopy. In contrast, high powered microscopy is not needed for standard IHC determination of hormone receptors in tumor tissue. These conventional methods of hormone receptor determination are thus unable to provide information regarding subnuclear PR distribution.

Progestins have complex actions in the breast and other hormone sensitive tissues by targeting distinct cells and having indirect effects on cells not expressing the PR. PR foci complexes are not qualitatively the same in normal tissue and cancerous tissue, and they do not necessarily activate the same progesterone receptor associated genes. Available clinical data does not fully support the position that conventional techniques for identifying hormone receptor positive cells are predictive of anti-hormone efficacy, whether it be for anti-estrogen or anti-progestin directed treatments. Currently, the decision to utilize a hormone treatment (e.g., antiestrogens or aromatase inhibitors) for patients with breast cancer and other hormone sensitive tumors is based on the simple presence of hormone-receptors in tumor samples. The presence of hormone receptors (ER or PR) does not fully predict for response to hormone treatment, as only 50-60% of hormone-receptor positive tumor cases are expected to benefit from treatment.

There is a need for a consistent method for predicting the efficacy of ONA and other anti-progestins with respect to heterogeneous "naturally occurring" tumors. Further, there is a need for an assay which is predictive of therapeutic efficacy of ONA and other anti-progestins against the cancers in individual patients.

SUMMARY

An important question pertinent to anti-progestin treatment is how to identify activated PRs that are relevant clinical therapeutic targets. The present exemplary methods are aimed at characterizing PRs that are present in a functional (activated) state in the human tumor tissue routinely obtainable in the clinical setting. As antagonizing non-active PR with a specific anti-progestin is therapeutically pointless, the present methods provide new and critical information to guide treatment of patients with anti-progestins. Such a predictive diagnostic test would provide (1) consistent methods to support therapeutic decision-making with respect to ONA and other anti-progestins, (2) guide selection of individual patients and patient populations that are likely to respond to treatment, and (3) exclude those individual patients that are least likely to respond or benefit from an anti-progestin treatment.

In one aspect, a method for identification and treatment of a subset of progesterone receptor (PR) positive tumors most susceptible to treatment with an anti-progestin such as onapristone (ONA) is provided. Progesterone receptor positive tumors exhibiting a dense, focal PR nuclear distribution pattern, as described herein, are more susceptible to treatment with anti-progestins such as onapristone. Results from in vitro homogeneous, experimental models are not necessarily predictive of the properties of naturally-occurring heterogeneous tumors.

In another aspect, a method of inhibiting the growth of a tumor susceptible to growth inhibition by anti-progestins is provided. A tissue sample suspected of being tumorigenic or cancerous can be obtained from a patient. Progesterone receptor positive cells in the tissue sample can be identified. The degree of distribution of the progesterone receptor foci in nuclei of the progesterone positive cells from the tissue sample can then be determined and an anti-progestin can be administered to the patient if the degree of focal distribution in the tissue sample is greater than about 5% of the progesterone receptor positive cells.

These patients are more likely to benefit from treatment with an anti-progestin that inactivates activated progesterone foci (APF) (e.g., ONA) and prevents further formation of APF than patients whose tumors do not express activated PR. The non-activated form of the PR is typically seen as diffuse nuclear PR staining. Inactivation of the APF by an anti-progestin may occur by any of a variety of mechanisms, including dissociation of the foci and inhibition of activation of the foci without substantially altering their structure. In one aspect, APF formation can be inhibited or prevented by an anti-progestin through several mechanisms. For example, onapristone may not allow the individual progesterone receptors to dimerize and prevent the PR from being phosphorylated at the ligand phosphorylation sites. The PR-ONA complex may bind weakly, or not at all, to its target DNA segment (PREs) and fail to induce the chromatin remodeling which is a necessary process for DNA transcription. In another example, other anti-progestins may allow the PR to dimerize and form complexes with co-activators or co-repressors which do not induce DNA transcription.

In this example, DNA binding may occur at the PRE, but transcription does not occur. Identification of APF may inform the decision of any anti-progestin treatment as long as the agent interferes with the PR pathway. In one aspect, identification of APF determines the status of the PR pathway as activated or not. For example, the use of mifepristone, or any progestin that complexes with PR and binds to the DNA, could be informed by the identification of APF. The activity of other agents, including those which would inhibit PR phosphorylation and thus interfere with PR activation, would be predicted by the presence of APF in various cancers. Thus, identification of APF could be used to inform treatment recommendations for various classes of compounds which act by inhibiting the function of the PR.

Patient tumors that do not express activated PR foci (APE) may include those that are PR-negative by the conventional assay, or those that are PR-positive by the conventional assay. In one aspect, any tumor/cancer which exhibits APF is a candidate for treatment with such anti-progestins, including breast, brain, meningiomas, prostate, ovarian, endometrial, uterine leiomyoma, lung, and uterine cancers. Pulmonary leiomyomatosis which has yet to be formally classified as a cancerous condition would also be likely to benefit if APF is expressed in the abnormal tissue. In another aspect, benign tumors not manageable with standard treatment, but presenting APF, can be treated by an antiprogestin as the presence of APF indicates that the tumor is driven by aberrant activation of PR, i.e. by the progestin pathway.

Another aspect provides a method of treating patient with a tumor susceptible to growth inhibition by anti-progestins by obtaining a tissue sample suspected of being tumorigenic or cancerous from a patient and exposing the tissue to an anti-progesterone receptor antibody. Progesterone receptor positive cells in the tissue sample can be identified. The degree of focal binding distribution of the progesterone receptor in nuclei of cells from the tissue can be determined. If the focal binding distribution is greater than about 5% of the progesterone receptor positive cells in the tissue sample, an anti-progestin is administered to the patient in a dosage range of about 10 to about 200 mg per day depending upon the potency, bioavailability, and safety profile of the antiprogestin.

In another aspect, the tissue is a specimen of a tumor tissue selected from the group consisting of breast, brain, meningiomas, prostate, ovarian, endometrial, uterine leiomyoma, lung, and uterine tissue.

In another aspect, the presence or absence of focal distribution is detected by fluorescence, a colorimetic reaction (e.g., an enzymatic reaction), imaged with a counter staining antibody (e.g., chromophore), radioactivity, and Western blot (e.g., differential phosphorylation of the PR).

In yet another aspect, the anti-progestin is selected from the group consisting of onapristone, lonaprisan, mifepristone, PF-02413873, telapristone, lilopristone, ORG2058, asoprisnil, and ulipristal.

The presence of active progesterone receptor focal distribution is indicated by a degree of nuclear focal distribution of greater than about 5% of the progesterone receptor positive cells. In another aspect, a tumor may be heterogeneous with respect to focal distribution and exhibit an active binding pattern (A) with distinct progesterone receptor foci, a diffuse binding pattern (D) without distinct progesterone receptor foci, or a mixture of an A pattern and a D pattern (AD) in various areas of the tumor.

In any of the foregoing aspects, when focal distribution (A or AD pattern) is present, the intensity or density of such focal distribution may be quantitated. For example, progesterone receptor antibodies may be radiolabeled, fluorescently labeled, imaged with a counter staining antibody (chromophore), imaged with a colorimetic reaction (e.g., an enzymatic reaction), or labeled in another manner where the intensity of the label can be measured and quantified.

DETAILED DESCRIPTION

Before describing several exemplary aspects described herein, it is to be understood that the invention is not limited to the details of construction or process steps set forth in the following description. The aspects described herein are capable of being practiced or being carried out in various ways.

As used herein, the phrases "treating a tumor" and "treatment of a tumor" mean to inhibit the replication of tumor cells, inhibit the spread of the tumor, decrease tumor size, lessen or reduce the number of tumor cells in the body, or ameliorate or alleviate the symptoms of the disease caused by the tumor, decrease the growth of the tumor (increase the time it takes the tumor to progress) or improve the survival of the patient when death is due to the cancer or secondary effects of the cancer. The term also includes treatment of cancer. Tumors include both cancers and non-cancerous tumors. The treatment is considered therapeutic if there is a decrease in mortality and/or morbidity, improvement of tumor-related symptoms, or there is a decrease in disease burden as may be manifested by reduced numbers of tumor cells in the body, decreased tumor size or improvement in the time to progression, improvement of progression free survival or improvement of disease free survival.

As used herein, the term "APF-active anti-progestin" and its equivalents refer to an anti-progestin drug which exhibits an ability to dissolve or dissociate activated PR foci (APF) in the nuclei of cells or inhibit the formation of APF in the nuclei of cells, indicating that its mechanism of action is via the PR activation pathway of the cell.

The terms "APF-positive", "PR foci positive", "activated PR", "PRs in a functional state" and the like refer to the presence of progesterone receptor aggregates in the nuclei of cells.

The term "focal distribution" refers to the distribution of "foci" (i.e., aggregation of progesterone receptors) in the nuclei of progesterone positive cells. Speckled or hyperspeckled pattern are terms that can be used referring to steroid nuclear receptor foci pattern in biology.

The term "degree of focal distribution" refers to the relative amount of PR foci present in the nuclei of progesterone positive cells. The degree of focal distribution can be determined quantitatively or qualitatively.

For example, the use of a colorimetric, enzymatic, or radiolabeled ligand such as a progesterone receptor antibody, can be used to bind to progesterone receptors in cell nuclei. The degree of focal distribution can be determined quantitatively, for example, by measuring color intensity, fluorescence or quantifying the level of radioactivity emitted by the labeled antibody. The degree of focal distribution can determined qualitatively by comparing the intensity of binding between a control sample and a labeled sample using a light microscope at an appropriate magnification or techniques including, but not limited to, DNA microarray, protein profiling, radiolabeling, or other surrogates for measuring APF.

The term "diffuse pattern" refers to a finely granular pattern which is indicative of the absence of focal distribution.

The term "progestin" refers to a natural or synthetic progestational substance that mimics some or all of the actions of progesterone, also referred to as progesterone receptor modulators (PRM) or selective progesterone receptor modulators (SPRM).

The term "anti-progestin" refers to a substance that inhibits the formation, transport, or action of or inactivates progestational agents, including, but not limited to, onapristone, lonaprisan, mifepristone, PF-02413873, telapristone, lilopristone, ORG2058, asoprisnil, and ulipristal. A PRM or SPRM may have some anti-progestin properties, and be considered an anti-progestin or a progestin depending on the context of use.

The term "antibody" or "antibodies" refers to a protein which is capable of specifically binding to an antigen and includes any substance, or group of substances, which has a specific binding affinity for an antigen to the exclusion of other substances. Generally, the term "antibody" includes polyclonal antibodies, monoclonal antibodies, antibodies derived from humans or animals, humanized antibodies (e.g., non-binding portions derived from a human, binding portions derived from an animals) and fragments thereof.

The terms "anti-PR-A" and "anti-PR-B" antibodies refer to antibodies directed to isoforms of the progesterone receptor—PR-A and PR-B respectively. Anti-PR-AB"refers to an antibody capable of binding to both PR-A and PR-B. Specific antibodies suitable for use in accordance with aspects herein include, but are not limited to, PgR636 and PgR1294 (M. Press, et al. (Steroids (2002) 67:799-813)), Novacastra clone 16, clone SAN27, clone 1A6, Dako clone PgR636, Ventana, clone 1E2, Novus Biologicals Progesterone Receptor [p Ser162] Antibody Clone 1064-E2; Novus Biologicals Progesterone Receptor [p Ser190] Antibody Clone EP1516Y, Novus Biologicals Progesterone Receptor [p Ser294] Antibody Clone 608, Abcam Progesterone Receptor [p Ser400] Antibody Ref ab60954, and Genetex Progesterone Receptor [p Ser554] Antibody Ref. GTX118987.

The term "administer" refers to providing a drug or drugs, prescribing one or more drugs, or placing one or more drugs on a formulary. The term "providing" refers to dispensing the drug directly to patient through any suitable route of administration (e.g., oral, injection, intravenous, intramuscular, and transdermal etc.) or providing instructions to a patient to do the same.

One aspect provides a method of inhibiting the growth of a tumor susceptible to growth inhibition by anti-progestins by obtaining a tissue suspected of being tumorigenic from a patient and determining the degree of focal distribution of anti-progesterone receptor in nuclei of cells from the tissue. If the degree of focal distribution is greater than about 5%, an ant-progestin (e.g., onapristone, lonaprisan, mifepristone, PF-02413873, telapristone, lilopristone, ORG2058, asoprisnil, and ulipristal) can be administered to the patient.

While the role of PR, progestins and anti-progestins in breast and other cancers has previously been studied, the results have been inconclusive leading to difficulties in diagnosing and treating patients. Multiple models have shown the numerous and complex interactions of species, strains, cancer type, carcinogens, and tumor environment among other factors. Without being bound by theory, the PR may be pathologically activated with altered physiological properties affecting the activation potential of the ligand resulting in abnormal or uncontrolled stimulation of cell growth and proliferation. However, the most commonly studied models originate from a small number of original tumors, and therefore do not accurately represent the physiological variability between tumor types or the tumors of different patients. That is, the limited number of cancer models is insufficient to cover the complexity of heterogenic cancers in a human population.

Studies of the formation of PR foci have been used to test compounds for their ability to induce PR translocation from the cytoplasm to the nucleus in genetically engineered cell lines. These assays, such as the Thermo Scientific PR (Progesterone Receptor) Redistribution Assay, use image analysis and fluorescence microscopy to quantitate nuclear accumulation of PR in the presence of the test compound. In contrast, aspects provided herein are designed for analysis of PR foci in primary tumor tissue, irrespective of the presence of a PR ligand or a drug. In one aspect, the exemplary methods described herein relate to the presence of PR foci in the nuclei of cells in naturally-occurring tumors indicating an anomaly that can be used to predict the efficacy in that patient of an anti-progestin that has PR antagonist properties. In another aspect, the characterization of constitutively activated PR in the clinic has now been found to indicate that tumors and cancers are susceptible to treatment with anti-progestins, including onapristone.

Onapristone, (e.g., (8S,11R,13R,14S,17S)-11-[4-(dimethylamino)phenyl]-17-hydroxy-17-(3-hydroxypropyl)-13-methyl-1,2,6,7,8,11,12,14,15,16-decahydrocyclopenta[a]phenanthren-3-one) has the following chemical structure:

Other anti-progestins include: progestational 3-(6,6-ethylene-17B-hydroxy-3-oxo-17A-pregna-4-ene-17A-YL)propionic acid G-lactones, 3-(6,6-ethylene-17.beta.-hydroxy-3-oxo-17.alpha.-pregna-4-ene-17.alpha.-y-l)propionic acid.gamma.-lactone and the following:

Mifepristone

(10S,11S,14S,15S,17R)-17-[4-(dimethylamino)phenyl]-14-hydroxy-15-methyl-14-(prop-1-yn-1-yl)tetracyclo[8.7.0.0^{2,7}.0^{11,15}]heptadeca-1,6-dien-5-one

Lilopristone
(11-beta,17-beta,17(z))-ropenyl);estra-4,9-dien-3-one,11-(4-(dimethylamino)phenyl)-17-hydroxy-17-(3-hydroxy-1-p;11β-[4-(Dimethylamino)phenyl]-17β-hydroxy-17-[(Z)-3-hydroxy-1-propenyl]estra-4,9-dien-3-one

ORG2058
(8R,9S,10R,13S,14S,16R,17S)-16-ethyl-17-(2-hydroxy-acetyl)-13-methyl-2,6,7,8,9,10,11,12,14,15,16,17-dodecahydro-1H-cyclopenta[a]phenanthren-3-one

Lonaprisan
(8S,11R,13S,14S,17S)-11-(4-acetylphenyl)-17-hydroxy-13-methyl-17-(1,1,2,2,2-pentafluoroethyl)-1,2,6,7,8,11,12,14,15,16-decahydrocyclopenta[a]phenanthren-3-one

Asoprisnil
(8S,11R,13S,14S,17S)-11-[4-[(E)-hydroxyiminomethyl]phenyl]-17-methoxy-17-(methoxymethyl)-13-methyl-1,2,6,7,8,11,12,14,15,16-decahydrocyclopenta[a]phenanthren-3-one Ulipristal
(8S,11R,13 S,14S,17R)-17-acetyl-11-[4-(dimethylamino)phenyl]-17-hydroxy-13-methyl-1,2,6,7,8,11,12,14,15,16-decahydrocyclopenta[a]phenanthren-3-one PF-2413873
4-[3-Cyclopropyl-1-(mesylmethyl)-5-methyl-1H-pyrazol-4-yl]oxy,-2,6-dimethylbenzonitrile In another aspect, focal PR binding provides a more sensitive and predictive test than currently-used conventional PR assays. Patients classified in conventional PR assays as PR-negative as well as those that are conventionally PR-positive may test positive for focal PR nuclear binding and therefore be candidates for treatment with anti-progestins such as onapristone. Thus, a patient previously identified as PR negative using previous methods would not have been considered a candidate for treatment with anti-progestins such as onapristone. The presence of PR foci in patients conventionally tested as PR-negative would explain the apparently anomalous result that onapristone is active in some of these patients. Aspects described herein will therefore make hormonal treatment potentially available to a greater number of patients with cancer, including potentially those patients with breast cancer that are classified as "triple negative" (i.e., negative for estrogen receptor (ER), PR and Her2).

Exemplary suitable immunohistochemical methods for use in aspects described herein are described by M. Press, et al. (Steroids (2002) 67:799-813) and M. Nadji (Anatomic Pathol. (2005) 123:21-27) hereby incorporated by reference in their entirety. By way of example, primary cancer tissue specimens for analysis may be prepared as paraffin sections or fine needle aspiration smears of the cancer tissue as is known in the art for conventional PR assays. If paraffin sections are used, the paraffin is first melted by heating the slides, and dewaxed with xylene. Slides are then rehydrated in decreasing grades of ethanol and exposed to an antibody, preferably a monoclonal antibody that specifically binds to PR-A, PR-B, or both. Binding of the antibody is then detected using any one of the methods known in the art for detection of antibody binding, examples of which are described below.

One exemplary suitable method for detection of binding of an antibody to its target is a colorimetric assay, typically an enzymatic colorimetric assay. One such method employs peroxidase to produce a colored stain visible under the light microscope. Endogenous peroxidase in the tissue specimen is blocked using hydrogen peroxide and endogenous biotin is blocked using a biotin-blocking reagent prior to incubation with the antibody or antibodies. If the primary antibody is a mouse antibody, it is subsequently bound to a biotinylated antimouse immunoglobulin. Streptavidin-peroxidase conjugate is added to bind the enzyme to the antibody-target complex. Color is developed by addition of diaminobenzidine and cupric sulfate. The tissue specimen may be counterstained with fast green to increase visibility of the peroxidase stain.

Alternatively, a fluorescence method may be used to detect antibody binding to PR-A, PR-B or both. In this case, a fluorescently-labeled primary antibody may be bound to the PR target and detected directly under a fluorescence microscope. However, a method employing binding of an unlabeled primary antibody to the PR followed by binding a fluorescently-labeled secondary (e.g., antimouse immunoglobulin) antibody to the primary antibody may reduce non-specific fluorescence. Any fluorescent label known for use in immunohistochemical assays may be used in the aspects described herein, for example FITC (fluorescein isothiocyanate); fluorescein FITC 520 nm green Alexa 488 515 nm green phycoerythrin PE 565 nm yellow; phycoerythrin-Texas Red ECD 620 nm red; phycoerythrin-cyanine-5 PC5 665 nm deep red; Peridinin chlorophyll PerCP 670 nm deep red; phycoerythrin-cyanine 5.5 PC5.5 703 nm far red; phycoerythrin-cyanine 7 PC7 755 far red; E allophycocyanin APC 660 nm deep red; Allophycocyanin-cyanine 7 APC-CY7.

Both monoclonal and polyclonal antibodies may be useful in aspects described herein. A non-exhaustive list of suitable monoclonal antibodies is described by M. Press, et al. supra, including two antibodies which are resistant to formalin fixation and paraffin embedding (PgR636 and PgR1294). Specific antibodies suitable for use in accordance with aspects herein include, but are not limited to, PgR636 and PgR1294 (M. Press, et al. (Steroids (2002) 67:799-813)), Novacastra clone 16, clone SAN27, clone 1A6, Dako clone PgR636, Ventana, clone 1E2, Novus Biologicals Progesterone Receptor [p Ser162] Antibody Clone 1064-E2; Novus Biologicals Progesterone Receptor [p Ser190] Antibody Clone EP1516Y, Novus Biologicals Progesterone Receptor [p Ser294] Antibody Clone 608, Abcam Progesterone Receptor [p Ser400] Antibody Ref ab60954, and Genetex Progesterone Receptor [p Ser554] Antibody Ref. GTX118987.

In one aspect, binding of the antibody to PR is detected by observation of the stained slide under a light microscope or fluorescence microscope as appropriate. Magnification is typically about 200× or 400× to evaluate, for example, the percentage of cells positive for binding to an antibody. However, to improve sensitivity for detection of APF it may be desirable to evaluate the slides at 800×-1000× to facilitate study of subnuclear structures.

Samples that are apparently PR negative by microscopy may be evaluated by flow cytometry to detect positive samples below the threshold of light or fluorescence microscopy. If flow cytometry indicates rare positive cells, high magnification X800-X1000 microscopy may be used to study subnuclear structures and identify activated progesterone receptor foci (APF). However, if the positive cells detected by flow cytometry are too rare to be reliably detected by microscopy for analysis of APF, a fluorescence-activated cell sorter (FACS) can be used to separate positive cells from the cells in suspension based on their fluorescence (e.g., Sony Cell Sorter SH800, Siemens Immulite 2000). As positive cells are concentrated but not damaged by this process, the reliability and probability of successfully visualizing APF on subsequent microscopic evaluation is substantially increased.

The presence or absence of APF in individual tumor cell nuclei may be detected visually under a light or fluorescence microscope, or by any other appropriate means, such as fluorescence or colorimetric measurements. In one aspect, visual means for detection will be used. The results of staining may be quantitated by noting presence or absence of APF, or by counting the number or percentage of positive cells. Alternatively, specific characteristics of the staining may be quantitated. For example, detection may include notation of whether or not focal binding in the form of APF is accompanied by diffuse nuclear staining, quantitation of positive cells by number or percentage, and/or quantitation of intensity or number/density of APF. Quantitation of APF density may be determined as the average number of foci/cell, or using an arbitrary scale (e.g., "few", "moderate" or "many"). Intensity may similarly be determined using an arbitrary scale, e.g., low/medium/high or a numerical scale such as 1-5. In another aspect, the results of the analysis of the patient's tumor tissue will be compared to positive and/or negative controls.

In one aspect, a tumor tissue specimen is judged as APF-positive when 1-100%, 5-100%, 25-100% or 50-100% of the nuclei of progesterone positive cells in the specimen exhibit APF. In yet another aspect, the therapeutic efficacy of an APF-active anti-progestin may also be correlated with the intensity of APF staining or with the number or density of APF, these parameters may also be used to determine the sensitivity of the tumor to treatment with the APF-active anti-progestin. In general, and without being bound by theory, the sensitivity of a tumor to treatment with APF-active anti-progestin will increase with increasing number or percentage of positive cells, increasing intensity of APF and/or increasing number of APF in the cells of the tumor tissue specimen.

In further aspects, methods for determining the sensitivity of a tumor to APF-active anti-progestins may be either manual (e.g., visual detection using a fluorescence microscope) or they may be automated or semi-automated using methods for rapid scanning, detection and quantitation of colorimetrically- or fluorescently-labeled tissue specimens. For example, a fully automated scanning and analysis system may be developed and used in certain aspects. While manual selection of specific regions of the tumor to be analyzed may be used in one aspect, (e.g., InScape® immunohistochemistry system ((e.g., InScape® immunohistochemistry system (Quest Diagnostics 3 Giralda Farms Madison, N.J. 07940), an automated system for scanning and analysis of APF in cell nuclei can be used to provide automated whole-specimen scanning and analysis of the antigen-specific immunohistochemistry stained specimen. In another aspect, image recognition can be used to create a digital image of the entire stained tissue section. An antigen-specific computer algorithm can be used to analyze the results of the digital image representing the whole specimen. In yet another aspect, the software can configured to distinguish foci from diffuse background staining in the nucleus, and measure fluorescence intensity and size of foci on a cell-by-cell or cluster-by-cluster basis, repeating the process for each cell or cluster over the entire specimen. These automated methods can, in certain aspects, result in improved accuracy by performing a function that is not possible manually, with reduced cost. Full automation can also make the test accessible to non-expert medical centers.

In one aspect, the decision whether to treat the patient based on the results of the diagnostic assay is based on the number/percentage, intensity and/or density of APF when they are present. Without being bound by theory, it is anticipated that the efficacy of treatment with an APF-active anti-progestin will increase with increasing number or percentage of positive cells, increasing intensity of APF and/or increasing number of APF in the cells of the tumor tissue specimen. Based on these parameters the medical practitioner may also determine the dosing, timing and length of treatment. Accordingly, another aspect relates to use of an APF-active anti-progestin for treating an APF-positive tumor.

The tumor to be identified or treated according to the above methods may include any cancerous or non-cancerous tumor in which APF occur, and in which the presence of APF can be determined. Such cancers or tumors include breast cancer, lung, uterine cancer, uterine leiomyoma, ovarian cancer, prostate cancer, brain, and angiomas. Benign tumors which can be identified or treated according to certain aspects include meningiomas, 70% of which express PR by conventional analysis.

The APF-active anti-progestin of the foregoing methods may be any anti-progestin drug having the ability to inactivate APF (for example by dissolving or dissociating the aggregates or preventing formation of APF or forming inactive APF). Such drugs include onapristone (ONA), but others with a similar mechanism of action are also suitable for use in aspects described herein.

Another aspect provides methods of identifying a tumor susceptible to growth inhibition by anti-progestins by obtaining a tissue suspected of being tumorigenic or cancerous from a patient and exposing the tissue to an anti-progesterone receptor antibody. Progesterone positive cells in the tissue sample can be identified. The degree of focal distribution of the progesterone receptor in nuclei of the progesterone positive cells from the tissue sample can be determined and an antiprogestin can be administered to the patient if the degree of focal distribution in the tissue sample is greater than about 5% of the progesterone receptor positive cells.

In yet another aspect, a method of treating a patient with a tumor susceptible to growth inhibition by anti-progestins is provided. The method comprises obtaining a tissue sample suspected of being tumorigenic from a patient and exposing the tissue to an anti-progesterone receptor antibody. The progesterone receptor positive cells in the tissue sample can be identified and the focal binding distribution of the progesterone receptor in nuclei of cells from the tissue can be determined. If the focal binding distribution is greater than 5% A or AD binding pattern of the progesterone receptor positive cells in the tissue sample, an anti-progestin is administered to the patient in a dosage range of about 10 to about 200 mg per day depending upon the potency, bioavailability, and safety profile of the anti-progestin.

In another aspect, the degree of focal distribution can be determined by suitable method as discussed herein including immunochemical, immunofluorescence, DNA microarray, protein profiling, radiolabeling, or other surrogates for measuring APF.

In another aspect, the tumor tissue is selected from the group consisting of breast, meningiomas, prostate, ovarian, endometrial, uterine leiomyoma, lung, and uterine tissue.

In yet another aspect, the anti-progestin is selected from the group consisting of onapristone, lonaprisan, mifepristone, PF-02413873, telapristone, lilopristone, ORG2058, asoprisnil, and ulipristal.

In another aspect, the degree of focal distribution is determined by identifying the binding pattern of progesterone receptor in the nuclei of progesterone positive tissue cells. Heterogeneous tumors include cells which may have active progesterone receptor foci or inactive progesterone receptor foci. Therefore, there may be cellular regions containing active foci as shown by distinct clumps in the cellular nuclei, and cellular regions which exhibit a more diffuse pattern.

Figure 1A:
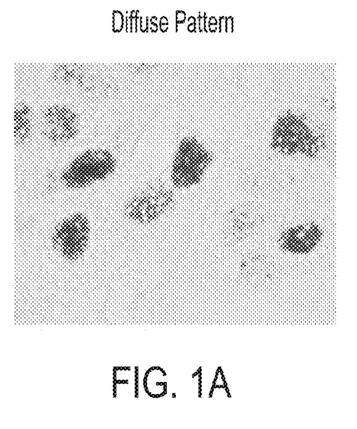
FIGS. 1A and 1B shows exemplary immunohistochemical brown nuclear staining patterns in human breast cancer samples derived from formalin-fixed and paraffin-embedded biopsies using antibodies directed to the progesterone receptor.
Figure 1B:
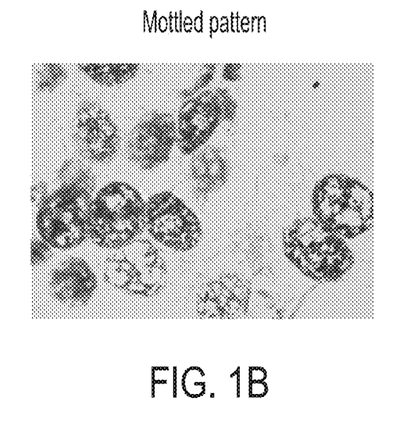

For example, FIG. 1 depicts two exemplary binding patterns from brown nuclear staining obtained with anti-progesterone antibodies in human breast cancer samples formalin-fixed and paraffin-embedded tissue samples obtained from biopsies of breast cancer patients. FIG. 1A shows a diffuse, granular pattern (D) indicative of cells which are not likely to be susceptible to treatment with anti-progestins. In contrast, FIG. 1B shows a mottled binding pattern (A) indicative of cells which are likely to be susceptible to treatment with anti-progestins. A mixed pattern exhibits both A and D patterns and is termed AD.

In another aspect, the anti-progesterone antibody is selected from the group consisting of anti-PR-A antibody, anti-PR-B antibody, and a mixture of anti-PR-A and anti-PR-B antibodies, and bispecific anti-PR AB antibodies.

In yet another aspect, the anti-progestin is administered in an amount from 10 to about 200 mg per day depending upon the potency, bioavailability, and safety profile of the anti-progestin. Without being bound by theory, it is believed that by identifying patients with tumors that are susceptible to treatment with progestins, a lower dose of the anti-progestin may be used resulting in a lower risk of toxic side effects. Thus, a lower dosage range can be used for patients exhibiting greater than 5% focal distribution of the progesterone receptor. In one aspect, the A or AD classification could result in different doses, while D pattern would indicate that treatment with an anti-progestin treatment is not warranted.

In yet another aspect, methods for screening antitumor drugs for the ability to inactivate APF are provided. These methods are useful, for example, to identify additional anti-progestins which may be candidates for use in treating of APF-positive tumors according to the methods described herein. In one aspect, the method provides a method of screening a drug candidate for the ability to decrease focal distribution of the progesterone receptor in the nuclei of progesterone receptor positive cells in a tumor. At least two tumor tissue specimens from the same tumor can be obtained. One tumor tissue specimen can be exposed to a drug candidate. The tumor tissue specimens can then be exposed to anti-progesterone receptor antibodies and the degree of focal distribution of progesterone receptors in the nuclei of the progesterone receptor positive cells from the tumor tissue specimens can be determined. If the focal distribution of the progesterone receptor in the tumor tissue specimen exposed to the drug candidate is decreased compared to tumor tissue specimens not exposed to the drug candidate, the drug candidate is capable of decreasing focal distribution of the progesterone receptor in progesterone receptor positive cells of the tumor.

Another aspect provides a system for classifying a tumor susceptible for treatment with an anti-progestin, comprising a tissue sample and at least one antibody or antibody binding fragment capable of detecting the progesterone receptor. The antibody or antibody binding fragment can be used to determine the degree of focal distribution of the progesterone receptor in the progesterone receptor positive nuclei of cells from a tumor tissue specimen. In another aspect, the tumor is susceptible to treatment with an anti-progestin if the degree of focal distribution in the cell nuclei of the progesterone positive cells is greater than about 5%.

In another aspect, detecting a decrease in detectable staining of the APF is an indication of APF inactivating activity of the antitumor drug. Detecting no substantial decrease in detectable staining of the APF is an indication of lack of APF inactivation of the antitumor drug.

In another aspect, an APF-active anti-progestin may be used in combination with additional hormonal treatment that does not act by an APF inactivation mechanism (e.g., antiestrogens) to achieve improved therapeutic efficacy as compared to either agent alone. Alternatively, an APF-active anti-progestin may be used in combination with one or more conventional chemotherapeutic agents which are negative for APF activity in the screening assay to achieve improved therapeutic efficacy as compared to either agent alone (e.g., everolimus, trastuzumab, TM1-D, anti-HER2 drugs, bevacizumab, or chemotherapy with agents such as paclitaxel, docetaxel, taxanes, doxorubicin, liposomal doxorubicin, pegylated liposomal doxorubicin, anthracyclines, anthracenediones, carboplatin, cisplatin, 5-FU, gemcitabine and cyclophosphamide). For example, everolimus is an mTor inhibitor that is indicated in combination with an aromatase inhibitor and may, in the future, be indicated in combination with an anti-progestin.

In yet another aspect, detecting the presence of focal distribution of the antibody to progesterone receptors in the nuclei may be used as an indication that the tumor of a patient previously treated with an antitumor drug, which has become resistant to that drug, is still sensitive to an APF-active anti-progestin such as onapristone. In one aspect, the method can be adapted to determine whether chemoresistance of a tumor resulting from previous chemotherapy can be reversed by treatment with an APF-active anti-progestin. Reversal of such chemoresistance may be based on the different mechanisms of action of the previous chemotherapy and the APF-active anti-progestin.

Another aspect is directed to a system for classifying a tumor susceptible for treatment with an anti-progestin. The system comprises a tissue sample and at least one antibody or antibody binding fragment capable of detecting the progesterone receptor wherein the antibody or antibody binding fragment is used to determine the degree of focal distribution of the progesterone receptor in the nuclei of cells from a tumor tissue specimen and wherein the tumor is susceptible to treatment with an anti-progestin if the degree of focal distribution is greater than about 5%.

EXAMPLE 1

Tumor specimens from patients with breast cancer (invasive ductal carcinoma) and endometrial cancer were selected from the archives of Oscar Lambret Cancer Center (Lille, France), anatomical pathological department. Patients had previously provided consent for the use of their tissues for research purposes. Samples of breast or endometrial tumor tissues which had been fixed in 4% formalin fixative and embedded in paraffin were obtained.

Immunohistochemistry (IHC) was performed on 3-4 µm sections of the archival breast or endometrial tumor tissues. The sections were deparaffinized, hydrated and washed in working buffer (0.05 mol/L Tris/HCl, 0.15 mol/L NaCl, 0.05% Tween 20, pH 7.6, Dako, Denmark, code S3006). Antigen retrieval was carried out with the Dako Target Retrieval Solution (modified citrate buffer, pH 6.1, Dako, Denmark, code 51699) in a water bath at 98° C. for 20 min. Then, the sections were covered with the Dako Peroxydase Block solution to block endogenous peroxides at room temperature (RT) for 5 min (Dako EnVision®+/HRP Mouse (DAB+) Kit, Dako, Denmark, code K4007), washed and incubated with the primary antibodies at the appropriate optimal dilutions at RT for 60 min in a humidified chamber (Table 1). Following a 5-min. wash with working buffer, the Dako Labelled Polymer (Dako EnVision®+/HRP Mouse (DAB+) Kit, Dako, Denmark, code K4007) was used for the detection of the primary antibody binding at RT for 30 min. Chromogen (DAB) was then used with Substrate-Batch at room temperature for 5-10 min and the sections were lightly counterstained with Gill's hematoxylin.

Negative controls were obtained by substitution of the primary antibodies with isotype control mouse IgG1 (Table 1) or with antibody diluent alone (wash buffer negative control) in the immunohistochemical staining procedure.

TABLE 1

Antibodies used for immunohistochemistry

| Antibody against | Clone | Dilutions | Host/ Isotype | Supplier | Code |
|---|---|---|---|---|---|
| PR, A form | 16 | 1:100 (3.6 µg/ml) 1:200 (1.8 µg/ml) | Mouse IgG1 | Novocastra | PGR-312-L-CE |
| PR, B form | SAN27 | 1:100 (0.4 µg/ml) 1:200 (0.2 µg/ml) | Mouse IgG1κ | Novocastra | PGR-B-CE |
| PR, A/B forms | 1A6 | 1:40 (1.2 µg/ml) 1:80 (0.6 µg/ml) | Mouse IgG1 | Novocastra | PGR-L-CE |
| PR, A/B forms | 16SAN27 | 1:100 (2 µg/ml) 1:200 (1 µg/ml) | Mouse IgG1 | Novocastra | PGR-AB-L-CE |
| Negative control | DAK-GO1 | 1:25 (4 µg/ml) 1:100 (1 µg/ml) 1:200 (0.5 µg/ml) | Mouse IgG1 | Dako | X0931 |

Immunohistochemistry analysis was performed using a Zeiss Axioscope microscope, equipped with an Imaging Model ROHS digital camera. Immunoreactive signals were classified as unequivocal brown labeling of tumor cell nuclei. The intensity of labeling was defined as 0 for negative, + for weak, ++ for moderate and +++ for strong.

EXAMPLE 2

12 breast cancer samples were analyzed with 3 different antibodies and 4 methods in IHC. 6 samples could be processed for further immunohistofluorescence (IHF) analysis.

Immunohistofluorescence was performed using a Zeiss fluorescent microscope equipped with a CCD camera and Smart Capture software, specific for capture of fluorescent images. IHF was performed on 3-4 μm sections of the archival breast tumor tissues. The sections were deparaffinized, hydrated and washed in working buffer (0.05 mol/L Tris/HCl, 0.15 mol/L NaCl, 0.05% Tween 20, pH 7.6, Dako, Denmark, code S3006). Antigen retrieval was carried out with the Dako Target Retrieval Solution (modified citrate buffer, pH 6.1, Dako, Denmark, code S1699) in a water bath at 98° C. for 20 min. Then, the sections were incubated with the primary antibodies at the appropriate optimal dilutions at RT for 60 min in a black humidified chamber (Table 2). Following a 5-minute wash with working buffer, appropriate secondary antibody conjugated to Alexa Fluor 488 was used for the detection of the primary antibody binding at RT for 30 min (Anti-mouse IgG (H+L), F(ab')2, Cell Signaling, USA, code 4408S, dilution 1:1000; Anti-rabbit IgG (H+L), F(ab')2, Cell Signaling, USA, code 4412S, dilution 1:1000). All slides were then washed and coverslipped using Vectashield® HardSet Mounting Medium (Vector Labs, USA, code H-1400) and stored refrigerate in the dark until analysis, to preserve fluorescence. Negative controls were obtained by substitution of the primary antibodies with isotype control mouse IgG1 or rabbit serum (see IHC table) or with antibody diluent alone (wash buffer negative control) in the immunohistofluorescence staining procedure.

All tumor samples were PR Positive for the three different antibodies. However, the analysis of the nuclear pattern was inconclusive in 6 out of 11 PR positive cases with the bispecific A and B antibody (1 case was PR negative with this antibody only). Six cases were subjected to IHF analysis with all of the antibodies. In two cases, the IHF procedure could not be performed with all antibodies because not enough tumor tissue remained available. The four cases could be analyzed with the PR B antibody.

The IHF analysis with the other antibodies (PRA and PRA+B) was inconclusive in one instance for characterizing the nuclear pattern. The IHF PR nuclear distribution and binding patterns observed were concordant with IHC.

Thereafter, a larger sample was analyzed in IHC with the Anti-PR A antibody, Anti-PR B antibody, or the mixture of both (called thereafter A+B).

75 breast cancers and 25 endometrial cancer samples were processed. For each labeled tumor sample, positive focal distribution was defined as the percentage of labeled tumor cells in the entire tumor tissue, excluding necrotic areas.

Figure 2A:
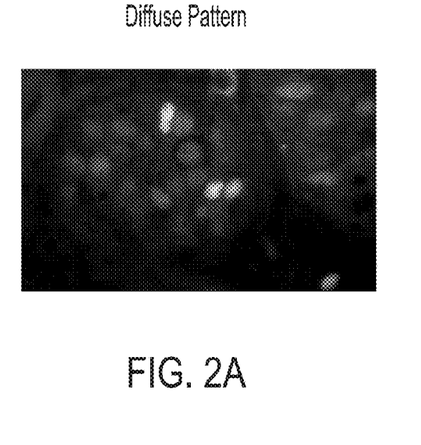
FIGS. 2A and 2B show exemplary green nuclear staining patterns in human breast cancer samples derived from formalin-fixed and paraffin-embedded biopsies using antibodies directed to the progesterone receptor.
Figure 2B:
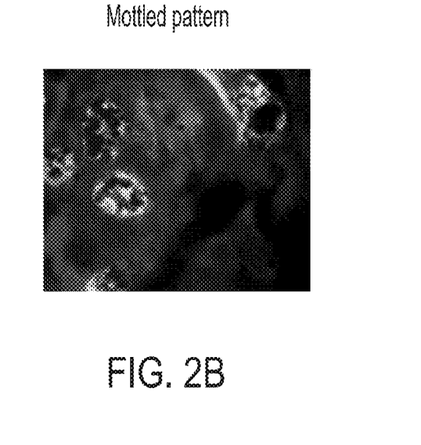

The two basic patterns found are presented in FIG. 1. These images show the staining of tissue samples with anti-PR antibodies using (1HC). FIG. 1A shows a brown, finely granular, and diffuse D pattern. FIG. 1B shows a mottled, clumped pattern representing a positive focal binding A pattern. FIG. 2 shows the same samples processed using IHF. FIG. 2A shows a diffuse D pattern similar to the IHC result in FIG. 2A. FIG. 2B shows a similar mottled, clumped, focal binding pattern as in FIG. 2B. The diffuse D pattern of FIGS. 1A and 2A are similar to the results obtained in gene-engineered cells that express a fluorescent receptor when no progesterone or no progesterone-agonist is present (Arnett-Manfield et Al, 2004, 1C Control, 1D, and 1E) and in normal human endometrial tissue and in endometrial cancer (Arnett-Manfield et Al, 2004, 1A, 1B, 1C, 1D, 1E, 1F).

The active A pattern observed in formalin fixed, paraffin embedded tumor tissue may differ from images obtained in fresh cells. This is expected because formalin-fixation and paraffin embedding tissue will result in changes to the cellular contents, thereby resulting in a different pattern of PR. Another difference relative to the research publications which utilized IHF, is related to the method. In the research setting, a confocal microscope (i.e. using two laser beams) provides high resolution and 3D images; thin slices of tissue samples (e.g., 2 microns) are utilized. The IHC pattern results from a chemical reaction that modifies the cellular content. In contrast for IHC, a traditional wide-field microscope is used for reading the standard thicker tumor slices (e.g., 4 microns). The IHC technique described results in some loss of resolution.

The IHF technique is less chemically aggressive for tumor tissues, in that it does not alter the microscopic cellular architecture. IHF requires specialized, equipment, a pathologist experienced with the technique, and is much more time-consuming. IHF cannot be easily coupled with other pathology analyses such as standard histology that requires formalin-fixed paraffin embedded tissues. Thus, in one aspect, 1HC may be used as a routine pathological laboratory procedure. In the developed IHC technique used herein, 4 micrometer tissue sections (a commonly used thickness for routine clinical analysis) were used for all analysis.

Figure 3A:
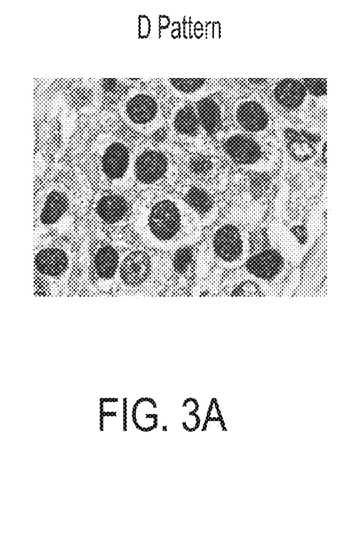
FIGS. 3A and 3B show exemplary immunohistochemical brown nuclear staining patterns with HES background counterstaining in human breast cancer samples derived from formalin-fixed and paraffin-embedded biopsies using antibodies directed to the progesterone receptor.
Figure 3B:
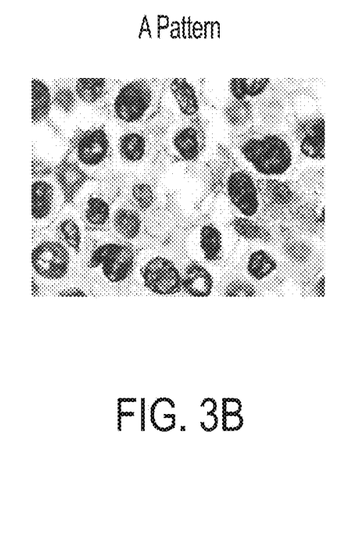

FIGS. 3A and 3B are equivalent to FIGS. 1A and 1B with background staining. The diffuse pattern observed in 5A, or in immunofluorescence, is darkened by the counterstaining. Likewise, 5B demonstrates gross nuclear anomalies. However, the even, diffuse pattern of 5A is still characteristic with 5A with homogeneous nuclei, while 1B translated in dysformed nuclei in 513.

Thus, two basic patterns are found: a diffuse PR nuclear staining indicating an absence of activated PRs, or and heterogeneous staining where aggregates, called PR foci, can be recognized within the nucleus of the cells. PR foci are larger than elements of a diffuse pattern that are substantially smaller (see Figures).

EXAMPLE 3

Three categories or phenotypes have been identified for use with aspects described herein and which are observed at higher magnification (800×). In contrast, standard magnification (400×) is used in for conventional IHC PR status determination.

Categories (observed at high magnification)

D: Diffuse Staining, no PR Foci (e.g., FIG. 1A)

AD: Area associating A and D cells, or heterogeneous distribution of PR foci with smaller sizes than A.

A Large Foci distributed in an heterogeneous manner (e.g., FIG. 1B)

This classification (D, AD, and A) was evaluated on 100 additional cases (75 breast cancer and 25 endometrial cancer tissue samples). In some cases the samples were positive for one PR isotype and not the other (e.g., positive for PR-A but not for PR-B).

Breast Cancer Samples (61 cases are analyzed for standard PR expression, 12 cases were PR negative for all antibodies, 2 cases had missing data).

TABLE 2

Breast Cancer Tumor Cells Positive for Indicated Antibody

| In Percentages | Number of Cases | Mean | Min | Max |
|---|---|---|---|---|
| Anti-PR A + B | 54 | 34% | 5% | 90% |
| Anti-PR A Alone | 51 | 31% | 5% | 90% |
| Anti-PR B Alone | 52 | 32% | 5% | 85% |
| Either A or B * | 58 | 36% | 5% | 95% |

* Each antibody gives statistically similar data with the same average percent (31-36%) of PR Positive cells and varying within the same range (5-95%).

* This is a computation that selects the highest percentage of PR A or PR B, as it was apparent that with the antibodies used, the rate of positive progesterone receptor cells was not the same for both antibodies in a same biopsy.

TABLE 3

Endometrial Cancer Cells Positive for Indicated Antibody
25 Cases (3 Negative Cases for All PR Antibodies)

| In Percentages | Number of Cases | Mean | Min | Max |
|---|---|---|---|---|
| Anti-PR A + B | 19 | 31% | 2% | 100% |
| Anti-PR A Alone | 18 | 21% | 5% | 90% |
| Anti-PR B Alone | 18 | 23% | 5% | 85% |
| Either A or B * | 20 | 27%% | 5% | 90% |

C. Focal Distribution

The section below describe the frequencies of A, AD, D patterns and N (negative, no PR staining). All cases were analyzed at high magnification (800×). Two breast cancer cases were not evaluable. The data in table 4 demonstrate that the classification varies with the antibody (PRA or PRB) used, and that there is more variability among the antibodies for the AD pattern. This most likely reflects the inherent deregulation of the two PR receptors (A and B) in cancer tissue. In certain aspects, antibodies targeted at each of the PR isoforms may be used to provide additional information for interpreting the results of the analysis. For example, a case may be "D" with an anti-PR A antibody and "AD" with the second anti-PR B antibody. Based on the later classification of "AD", a treatment with a anti-progestin would be potentially appropriate. Similarly, a case may be "A" with an antibody against PR A and "AD" with an antibody against PR B, which could potentially require a different (higher) dose of the anti-progestin because of the greater degree of malignant cell growth indicated by the aberrant PR activity. Conventional IHC methods to determine PR cannot provide this information because they only indicate the presence or absence of hormone receptors (i.e., ER and PR). In one aspect, the activated PR foci pattern based on analysis with 1 or more separate antibodies would provide additional information for analyzing the activated PR foci pattern.

TABLE 4

PR Focal Distribution for Breast Cancer Cells

| In Number of cases | Number of cases | A | AD | D | Neg |
|---|---|---|---|---|---|
| Anti-PR A + B | 71 | 4 | 21 | 29 | 17 |
| Anti-PR A Alone | 67 | 3 | 19 | 29 | 16 |
| Anti-PR B Alone | 69 | 1 | 24 | 17 | 27 |

TABLE 4-continued

PR Focal Distribution for Breast Cancer Cells

| In Percentages | % | A | AD | D | Neg |
|---|---|---|---|---|---|
| Anti-PR A and B | 101% | 6% | 30% | 41% | 24% |
| Anti-PR A Alone | 99% | 4% | 28% | 43% | 24% |
| Anti-PR B Alone | 100% | 1% | 35% | 25% | 39% |

EXAMPLE 4

In the data set outlined in the tables below, a given tumor sample could be APF negative for one antibody and APF positive for another and show a different APF pattern for one antibody versus the other antibody. However, the results were generally concordant between PR-A and PR-B antibodies. This concordance is shown on the diagonal of the cross-tabulations that follow below. The concordance between the two sets of conditions is highlighted in the shaded text box of the table. These results illustrate that in certain aspects, more than one antibody would provide additional information to identify the APF nuclear distribution pattern.

Table 5 below compares the APF patterns with the PR A antibody in relationship to the PR A+B antibody mixture in the breast cancer samples. A: Aggregated Pattern with large foci, AD: mix of A Cells and D cells, or heterogeneous medium-medium size foci. D: diffuse pattern or absence of Activated PR. The columns classify the cases according to the indicated binding pattern using only the PR-A antibody while the rows classify the cases using PR-A+PR-B antibodies. The diagonal, highlighted row shows the number of concordant cases, i.e., cases with the same binding pattern using both methods. Other cells show discordant results, i.e., cases with different binding patterns for each method.

TABLE 5

Comparison of the APF patterns with PR A versus PR A + B

| Breast Cancer | | PR A | | | | |
|---|---|---|---|---|---|---|
| | Total | A | AD | D | Neg | N/A |
| PR A + B Total | | 3 | 19 | 29 | 16 | 4 |
| A | 4 | | 2 | 0 | 0 | 0 |
| AD | 21 | 1 | | 6 | 2 | 0 |
| D | 29 | 0 | 5 | | 5 | 1 |
| Neg | 17 | 0 | 0 | 5 | | 3 |
| N/A | 0 | 0 | 0 | 0 | 0 | |

Table 6: Breast cancer samples: Cross-tabulation of results obtained with an anti-PR B antibody (PR B) vs the mixture of anti-PR A and anti-PR B (PR A+B). A: Aggregated Pattern with large foci, AD: mix of A Cells and D cells, or heterogeneous medium-medium size foci. D: diffuse pattern or absence of Activated PR. The columns classify the cases according to the indicated binding pattern using only the PR-B antibody while the rows classify the cases using PR-A+ PR-B antibodies. The diagonal, highlighted row shows the number of concordant cases, i.e., cases with the same binding pattern using both methods. Other cells show discordant results, i.e., cases with different binding patterns for each method.

TABLE 6

Comparison of the APF patterns with PR B versus PR A + B

| Breast Cancer | | PR B | | | | | |
|---|---|---|---|---|---|---|---|
| | | Total | A | AD | D | Neg | N/A |
| PR A + B | Total | 71 | 1 | 24 | 27 | 17 | 2 |
| | A | 4 | 1 | 3 | 0 | 0 | 0 |
| | AD | 21 | 0 | 14 | 5 | 2 | 0 |
| | D | 29 | 0 | 7 | 19 | 3 | 0 |
| | Neg | 17 | 0 | 0 | 3 | 12 | 2 |
| | N/A | 0 | 0 | 0 | 0 | 0 | 0 |

Table 7: Breast cancer samples: Cross-tabulation of results obtained with an anti-PR B antibody (PR B) vs an antibody anti-PR A (PR A). A: Aggregated Pattern with large foci, AD: mix of A Cells and D cells, or heterogeneous medium-medium size foci. D: diffuse pattern or absence of Activated PR. The columns classify the cases according to the indicated binding pattern using only the PR B antibody while the rows classify the cases using PR A antibody. The diagonal, highlighted row shows the number of concordant cases, i.e., cases with the same binding pattern using both methods. Other cells show discordant results, i.e., cases with different binding patterns for each method.

TABLE 7

Comparison of the APF patterns with PR A versus PR B

| Breast Cancer | | PR B | | | | | |
|---|---|---|---|---|---|---|---|
| | | Total | A | AD | D | Neg | N/A |
| PR A | Total | 71 | 2 | 24 | 17 | 27 | 1 |
| | A | 3 | 0 | 1 | 0 | 1 | 1 |
| | AD | 19 | 0 | 16 | 2 | 1 | 0 |
| | D | 29 | 0 | 5 | 4 | 20 | 0 |
| | Neg | 16 | 2 | 2 | 9 | 5 | 0 |
| | N/A | 4 | 0 | 0 | 2 | 0 | 0 |

Endometrial Cancer

Similar patterns of PR nuclear distribution are observed in endometrial cancer samples. Importantly, normal fibroblasts were found in biopsy samples and were noted to be PR positive. These normal fibroblasts had a D PR nuclear distribution phenotype indicating that the PR in these normal cells were not activated, most likely because the patients are post menopausal and thus are not producing physiologic levels of progesterone. Therefore, the fibroblasts are not exposed to endogenous progesterone. In contrast, cancer tissue was presenting activated form of PR (APF) even in absence of physiological progesterone as indicated by the fibroblast pattern.

Table 8: Endometrial cancer samples: Cross-tabulation of results obtained with an anti-PR A antibody (PR A) vs the mixture of Anti-PR A and an antibody Anti-PR B (PR A+B). A: Aggregated Pattern with large foci, AD: mix of A Cells and D cells, or heterogeneous medium-medium size foci. D: diffuse pattern or absence of Activated PR. The columns classify the cases according to the indicated binding pattern using only the PR A antibody while the rows classify the cases using PR A and PR B antibodies. The diagonal, highlighted row shows the number of concordant cases, i.e., cases with the same binding pattern using both methods. Other cells show discordant results, i.e., cases with different binding patterns for each method.

TABLE 8

Comparison of the APF patterns with PR A versus PR A + B

| Endometrial Cancer | | PR A | | | | | |
|---|---|---|---|---|---|---|---|
| | | Total | A | AD | D | Neg | N/A |
| PR A + B | Total | 23 | 0 | 12 | 5 | 6 | 0 |
| | A | 1 | 0 | 1 | 0 | 0 | 0 |
| | AD | 11 | 0 | 9 | 2 | 0 | 0 |
| | D | 4 | 0 | 0 | 3 | 1 | 0 |
| | Neg | 7 | 0 | 2 | 0 | 5 | 0 |
| | N/A | 0 | 0 | 0 | 0 | 0 | 0 |

Table 9: Endometrial cancer samples: Cross-tabulation of results obtained with an anti-PR B antibody (PR B) vs the mixture of Anti-PR A and an antibody Anti-PR B (PR A+B). A: Aggregated Pattern with large foci, AD: mix of A Cells and D cells, or heterogeneous medium-medium size foci. D: diffuse pattern or absence of Activated PR. The columns classify the cases according to the indicated binding pattern using only the PR B antibody while the rows classify the cases using PR A and PR B antibodies. The diagonal, highlighted row shows the number of concordant cases, i.e., cases with the same binding pattern using both methods. Other cells show discordant results, i.e., cases with different binding patterns for each method.

TABLE 9

Comparison of the APF patterns with PR B versus PR A + B

| Endometrial Cancer | | PR B | | | | | |
|---|---|---|---|---|---|---|---|
| | | Total | A | AD | D | Neg | N/A |
| PR A + B | Total | 23 | 0 | 16 | 4 | 3 | 0 |
| | A | 1 | 0 | 1 | 0 | 0 | 0 |
| | AD | 11 | 0 | 11 | 0 | 0 | 0 |
| | D | 4 | 0 | 2 | 0 | 2 | 0 |
| | Neg | 7 | 0 | 2 | 4 | 1 | 0 |
| | N/A | 0 | 0 | 0 | 0 | 0 | 0 |

Table 10: Endometrial cancer samples: Cross-tabulation of results obtained with an anti-PR B antibody (PR B) vs an antibody Anti-PR A (PR A). A: Aggregated Pattern with large foci, AD: mix of A Cells and D cells, or heterogeneous medium-medium size foci. D: diffuse pattern or absence of Activated PR. The columns classify the cases according to the indicated binding pattern using only the PR B antibody while the rows classify the cases using PR A antibody. The diagonal, highlighted row shows the number of concordant cases, i.e., cases with the same binding pattern using both methods. Other cells show discordant results, i.e., cases with different binding patterns for each method.

TABLE 10

Comparison of the APF patterns with PR B versus PR A

| Endometrial Cancer | | PR B | | | | | |
|---|---|---|---|---|---|---|---|
| | | Total | A | AD | D | Neg | N/A |
| PR A | Total | 25 | 0 | 17 | 5 | 3 | 0 |
| | A | 0 | 0 | 0 | 0 | 0 | 0 |
| | AD | 12 | 0 | 12 | 0 | 0 | 0 |
| | D | 6 | 0 | 4 | | 2 | 0 |
| | Neg | 7 | 0 | 1 | 5 | 1 | 0 |
| | N/A | 0 | 0 | 0 | 0 | 0 | 0 |

In one aspect, the use of antibodies directed to PR-A and PR-B or bi-specific antibodies directed to PR-A and PR-B can be used together to identify the AD pattern PR nuclear distribution pattern where use of a single antibody (e.g., PR-A or PR-B) may not identify the AD pattern in certain cases.

In another aspect, the methods disclosed herein describe a PR nuclear pattern in cancer biopsies shown using, for example, IHC, and confirmed using fresh tissues and IHF. The diffuse pattern is found in normal cells/tissues that are not exposed to progestins under experimental and physiological conditions. The diffuse nuclear distribution pattern indicates that the PR of the tumor cells is not activated, and therefore treatment of the tumor with an antiprogestin is unlikely to be effective. In contrast, the presence of the AD or A pattern is similar to what is observed when experimental models or normal cells are exposed to progestins. These patterns signal that PRs are activated and transcriptionally activate in some cells and that treatment with antiprogestins is likely to be effective in these cases.

Expression of these patterns (e.g., A and AD) is heterogeneous in tumors and across different samples, which is a characteristic of cancers. In contrast, the D phenotype is homogeneous, a pattern consistent with a lack of PR biologic function. The expression of PR and the phenotype we have described vary according to the expressed PR Isotype (A or B) and the antibody used (e.g., bispecific AB, A only, B only and the mixture of A+B). This variability of the PR nuclear distribution pattern is not unexpected in naturally occurring human cancers which are inherently heterogenous.

EXAMPLE 5

Figure 4:
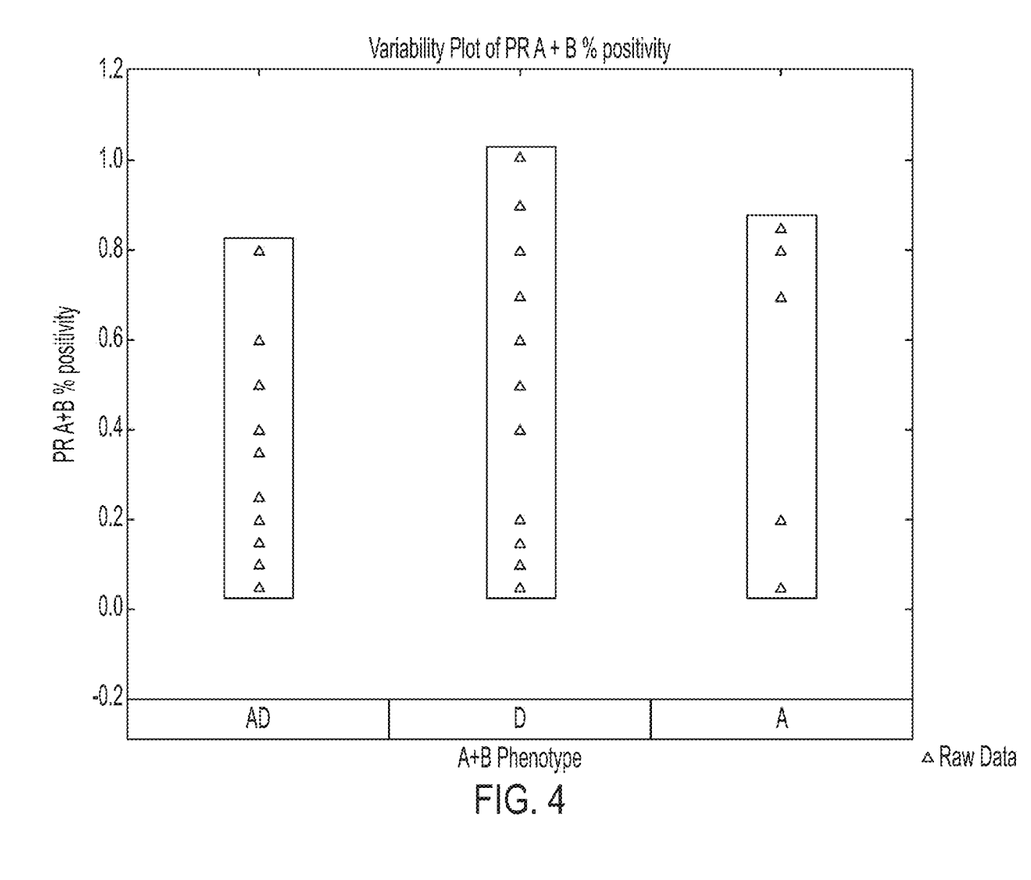
FIG. 4 shows the percent of breast cancer samples positive for PR-A and PR-B for three binding patterns, A, AD, and D.

The plot of FIG. 4 shows the percent of breast cancer samples positive for PR-A and PR-B for the three binding patterns, A, AD, and D. The results support the conclusion that a positive progesterone receptor status determined by conventional methods does not correlate with the presence of PRF distribution as described herein.

EXAMPLE 6

Table 11

Table 11 shows the percentage of "A" binding pattern cells for tissue samples exhibiting both "A" and "D" binding pattern cells. The column labeled "APR" indicates the overall pattern observed for the tissue sample while the "A %" column indicates the percentage of cells in the sample that exhibit the "A" binding pattern. Each row shows the results for one case using both anti-PR-A and anti-PR-B antibodies or each antibody alone.

TABLE 11

Percentage of Cells expressing the APF pattern with different antibodies

| PR A + B | | PR A | | PR B | |
|---|---|---|---|---|---|
| APR | % of Cells with APF | APR | % of Cells with APF | APR | % of Cells with APF |
| AD | 30% | AD | | AD | |
| A | | AD | 5% | AD | |
| D | | D | | AD | 5% |
| AD | | AD | 0% | AD | 20% |
| D | | AD | 0% | AD | 10% |
| AD | 10% | D | | AD | |
| A | | AD | 15% | A | |
| A | | AD | 40% | AD | 20% |
| A | | A | | AD | 10% |
| A | | AD | 20% | AD | 20% |
| AD | 50% | D | | D | |
| AD | 5% | AD | | D | |
| AD | 5% | D | | D | |
| AD | 70% | A | | AD | 40% |
| AD | 5% | D | | AD | |
| AD | 10% | Neg | | AD | 40% |
| AD | 60% | D | | AD | 10% |
| AD | 30% | AD | | D | |
| A | | AD | 20% | D | |
| AD | | AD | 20% | AD | |
| AD | 50% | AD | 30% | AD | 20% |
| A | | AD | 20% | AD | 20% |
| A | | A | | AD | 5% |

Although the invention herein has been described with reference to particular embodiments, it is to be understood that these embodiments are merely illustrative of the principles and applications of the present invention. It will be apparent to those skilled in the art that various modifications and variations can be made to the method and systems described herein without departing from the spirit and scope of the invention. Thus, it is intended that the present invention include modifications and variations that are within the scope of the appended claims and their equivalents.

What is claimed is:

1. A method of inhibiting the growth of a tumor susceptible to growth inhibition by anti-progestins, comprising:
    a) obtaining a tissue sample suspected of being tumorigenic or cancerous from a patient;
    b) identifying progesterone receptor positive cells in the tissue sample;
    c) determining the degree of focal distribution of the progesterone receptor in nuclei of the progesterone positive cells from the tissue sample and identifying the binding pattern of the progesterone positive cells of the tissue; and
    d) administering an anti-progestin to the patient if the degree of focal distribution in the tissue sample is greater than about 5% of the progesterone receptor positive cells, wherein the anti-progestin is selected from the group consisting of onapristone, lonaprisan, mifepristone, PF-02413873, telapristone, lilopristone, ORG2058, asoprisnil, and ulipristal.

2. The method of claim 1, further comprising determining the degree of focal distribution in nuclei in cells from the tissue by exposing the tissue to anti-progesterone receptor antibodies.

3. The method of claim 1, wherein the tumor is selected from the group consisting of breast, brain, meningiomas, prostate, ovarian, endometrial, uterine leiomyoma, lung, and uterine tissue.

4. The method of claim 1, wherein the binding pattern is selected from group consisting of diffuse (D), active (A), and active/diffuse (AD).

5. The method of claim 2, wherein at least two antibodies are used to determine the degree of focal distribution.

6. The method of claim 2, wherein the antibodies are selected from the group consisting of anti-PR-A antibody, anti-PR-B antibody, and a mixture of anti-PR-A and anti-PR-B antibodies, and bi-specific antibodies related to PR-A and PR-B.

7. The method of claim 2, wherein the degree of focal distribution of the progesterone receptor is determined by a detection method selected from the group consisting of immunohistochemistry, immunofluorescence, and Western blot.

8. The method of claim 1, wherein the anti-progestin is administered to the patient in an amount from about 10 mg to about 200 mg per day.

9. A method of treating a patient with a tumor susceptible to growth inhibition by anti-progestins, comprising:
 a) obtaining a tissue sample suspected of being tumorigenic from a patient;
 b) exposing the tissue to an anti-progesterone receptor antibody;
 c) identifying progesterone receptor positive cells in the tissue sample and identifying the binding pattern of the progesterone positive cells of the tissue;
 d) determining the focal binding distribution of the progesterone receptor in nuclei of cells from the tissue and identifying the binding pattern of the progesterone positive cells of the tissue, wherein if the focal binding distribution is greater than 5% of the progesterone receptor positive cells in the tissue sample with an A or AD binding pattern, an anti-progestin is administered to the patient in a dosage range of about 10 to about 200 mg per day, wherein the anti-progestin is selected from the group consisting of onapristone, lonaprisan, mifepristone, PF-02413873, telapristone, lilopristone, ORG2058, asoprisnil, and ulipristal.

10. The method of claim 9, wherein the tumor is selected from the group consisting of breast, brain, meningiomas, prostate, ovarian, endometrial, uterine leiomyoma, lung, and uterine tissues.

11. The method of claim 9, wherein the binding pattern is selected from group consisting of diffuse (D), active (A), and active/diffuse (AD).

12. The method of claim 9, wherein the antibody is selected from the group consisting of anti-PR-A antibody, anti-PR-B antibody, a bi-specific antibody directed to PR-A and PR-B, and a mixture of anti-PR-A and anti-PR-B antibodies.

* * * * *